United States Patent [19]

Robblee

[11] Patent Number: 4,717,581
[45] Date of Patent: Jan. 5, 1988

[54] IRIDIUM OXIDE COATED ELECTRODES FOR NEURAL STIMULATION

[75] Inventor: Lois S. Robblee, Norwood, Mass.

[73] Assignee: EIC Laboratories, Inc., Norwood, Mass.

[21] Appl. No.: 929,778

[22] Filed: Nov. 13, 1986

Related U.S. Application Data

[62] Division of Ser. No. 829,693, Feb. 6, 1986.

[51] Int. Cl.[4] ............................................. A61N 1/05
[52] U.S. Cl. ...................................... 427/2; 427/126.5
[58] Field of Search ................................. 427/2, 126.5

[56] References Cited

FOREIGN PATENT DOCUMENTS 1206863  9/1970  United Kingdom ............ 427/126.5

Primary Examiner—Sam Silverberg
Attorney, Agent, or Firm—Charles Hieken

[57] ABSTRACT

A metallic electrode made of platinum, platinum iridium alloy, stainless steel, stainless steel alloys, titanium, titanium alloys, tantalum or tantalum alloys is coated with iridium oxide. Ir(III) trichloride is heated in 5.5M HCl until 75–80% of the solution is evaporated. Isopropyl or ethyl alcohol is added to the evaporated solution to restore the solution to its original volume. This restored acid/alcohol solution is aged for 1–2 weeks. The metallic electrode is soaked in the aged acid/alcohol solution for 16 hours, dried for one hour at room temperature and annealed in air at 320° C. for 80–90 minutes.

6 Claims, 16 Drawing Figures

|—————|
10 microns

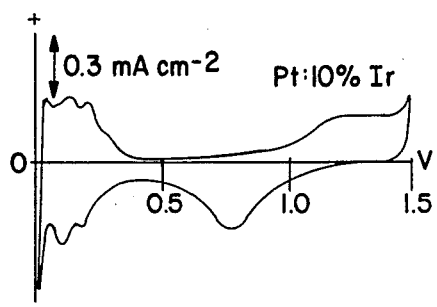
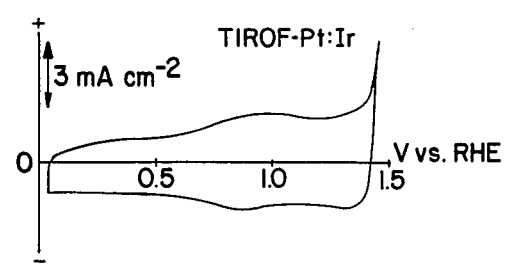
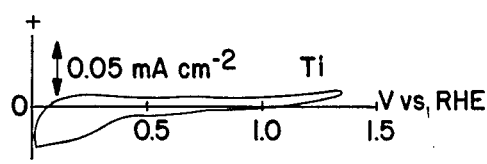
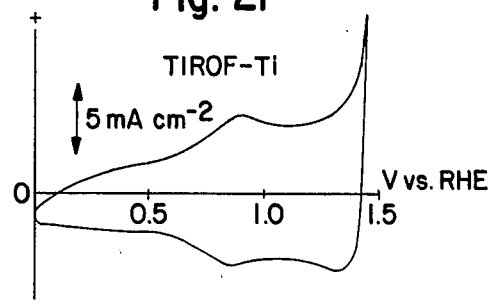
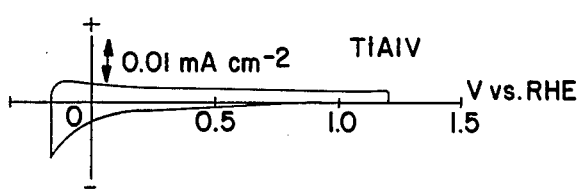
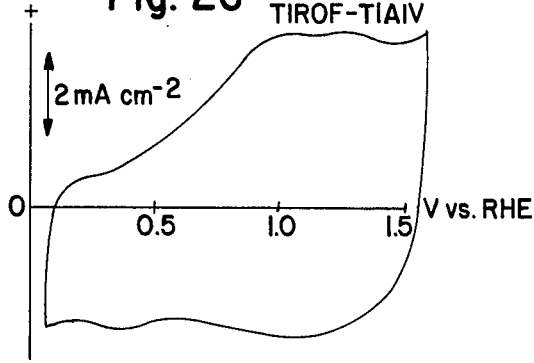
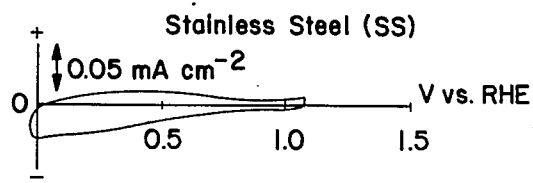
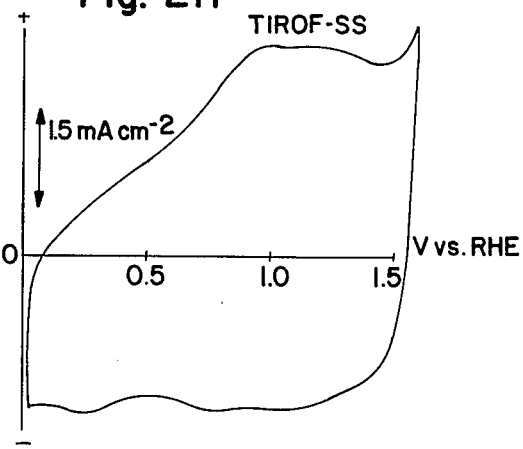
Fig. 2 Cyclic voltammetric behavior of uncoated metallic electrodes (A–D) and thermal Ir oxide (TIROF) coated metallic electrodes (E–H).
Electrolyte: 0.1M $H_2SO_4$ (A,B,E,F)
Physiological Saline (C,D,G,H)
Sweep Rate: 0.1V $sec^{-1}$ — Pt
····· Pt. 30% Ir
--- Ir - Deactivated
± 0.8 mC cm$^{-2}$
± 0.8 A cm$^{-2}$ TIROF-Pt:Ir
∓3.2 mC cm$^{-2}$
∓3.2 A cm$^{-2}$ TI
±0.8 mC cm$^{-2}$
±0.8 A cm$^{-2}$ TIROF-TI
±1.6 mC cm$^{-2}$
±1.6 A cm$^{-2}$ STAINLESS STEEL (SS)
∓0.04 mC cm$^{-2}$
∓0.2 A cm$^{-2}$ TIROF-SS
∓1 mC cm$^{-2}$
∓5 A cm$^{-2}$ Fig. 3 Voltage response of uncoated metallic electrodes (A-C) and thermal Ir oxide (TIROF) coated metallic electrodes (D-F) to biphasic current pulses.

IRIDIUM OXIDE COATED ELECTRODES FOR NEURAL STIMULATION

This application is a division of application Ser. No. 829,693, filed 2/6/86.

This invention relates in general to electrodes and more particularly to metallic electrodes with resistant interfaces used to inject charge into biological tissue with controlled current or voltage pulses. Such electrodes are used in electrical stimulation of excitable tissue elements of the body, e.g., nerve or muscle fibers. There follows a list of publications:

1. Brummer, S. B. and Turner, M. J., 1977. Electrochemical considerations for safe electrical stimulation of the nervous system with platinum electrodes. IEEE Trans. Biomed. Eng. BME-24:59.
2. Hambrecht, F. T., 1979. Neural prosthesis. Ann. Rev. Biophys. Bioeng. 8:239.
3. Brummer, S. B. and Turner, M. J., 1977. Electrical stimulation with Pt electrodes: II. Estimation of maximum surface redox (theoretical non-gassing) limits. IEEE Trans. Biomed. Eng. BME-24:440.
4. McHardy, J., Geller, D. and Brummer, S. B., 1977. An approach to corrosion control during electrical stimulation. Ann. of Biomed. Eng. 5:144.
5. Robblee, L. S., McHardy, J., Marston, J. M. and Brummer, S. B., 1980. Electrical stimulation with Pt electrodes. IV. The effect of protein on Pt dissolution. Biomaterials 1:135.
6. Robblee, L. S., McHardy, J., Agnew, W. F. and Bullara, L. A. 1983. Electrical stimulation with Pt electrodes. VII. Dissolution of Pt electrodes during electrical stimulation of the cat cerebral cortex. J. Neuroscience Methods 9:301.
7. Stoney, S. D. Jr., Thompson, W.D. and Asanuma, H., 1968. Excitation of pyramidal tract cells by intracortical microstimulation: Effective extent of stimulation current. J. Neurophysiol. 31:659.
8. Rose, T. L., Kelliher, E. M. and Robblee, L. S., 1985. Assessment of capacitor electrodes for intracortical neural stimulation. J. Neuroscience Methods 12:181.

Reference is made to a respective publication by parenthesizing the number preceding it.

Safe electrical stimulation of the nervous system requires reversible charge injection processes which utilize only double-layer capacitance and reversible faradaic processes confined to the electrode surface (1). Charge injection by any other faradaic reactions will be at least partially irreversible because products will tend to escape from the electrode surface. Irreversible faradaic reactions include water electrolysis, saline oxidation, metal dissolution, and oxidation of organic molecules.

The most commonly used materials for fabricating electrodes for electrical stimulation of nerves or muscles within the body are platinum (Pt), Pt alloys and stainless steel (2). These materials are known to have a limited range for "reversible" charge injection by surface faradaic processes in the in vivo saline environment before the onset of water electrolysis (ca. 0.5 mC/cm$^2$ for Pt and Pt alloys)(3) or catastrophic corrosion (ca. 0.04 mC/cm$^2$ for stainless steel)(4). These charge injection limits restrict their usefulness as stimulation electrodes to applications requiring only low charge injection densities. However, even low charge injection densities are known to produce corrosion of the metal, thereby releasing trace quantities of dissolved metal into the surrounding environment, and altering the interfacial properties between electrode and tissue (5,6). In the case of Pt or Pt alloy electrodes, dissolution products may be toxic to the tissue in which the electrodes are implanted. In the case of stainless steel electrodes, dissolution or corrosion of the electrode may result in electrode failure due to corrosion-induced fracture. In the case of very small electrodes such as might be used to stimulate a single neuron, dissolution might result in the disappearance of the entire electrode.

Some of the problems associated with the above electrode materials might be circumvented by the use of so-called "capacitor" electrodes, $Ta/Ta_2O_5$ or $Ti/TiO_2$, which inject charge via charging and discharging of a capacitor film, and thereby eliminate faradaic processes at the interface. However, a serious drawback to the utility of these capacitor electrodes is that they are limited to injecting anodic charge only, unless appropriately biased, whereas the physiological preference is for cathodic charge (7). In addition, their charge injection limits are lower than those of Pt or Pt alloys (8).

The present invention overcomes these disadvantages by means of a layer of iridium oxide deposited on the surface of the metallic electrode and intervening between the metallic surface adjacent to the deposited oxide and the biological tissue. The iridium oxide layer becomes the charge transfer interface and enables charge injection densities up to 10 mC/cm$^2$ for either cathodic or anodic polarities without water electrolysis or other faradaic reactions that are involved in corrosion of the underlying metallic electrode. The iridium oxide layer can be deposited on any metallic surface. Thus, electrode applications which have stringent mechanical or physical requirements, e.g., intramuscular electrodes, may utilize the metal having the desired physical properties and still benefit from the charge injection properties of iridium oxide.

Numerous other features, objects and advantages of the invention will become apparent from the following specification when read in connection with the accompanying drawing in which:

BRIEF DESCRIPTION OF THE DRAWING

FIG. 2 compares voltammetric curves of uncoated electrodes in FIGS. 2A–2D and electrodes coated with iridium oxide according to the invention in FIGS. 2E–2H.

DETAILED DESCRIPTION OF PREFERRED EMBODIMENTS

Figure 1B:
FIGS. 1A and 1B are scanning electron microscope photographs of a metallic electrode surface without and with respectively an iridium oxide layer on the surface.
Figure 1A:
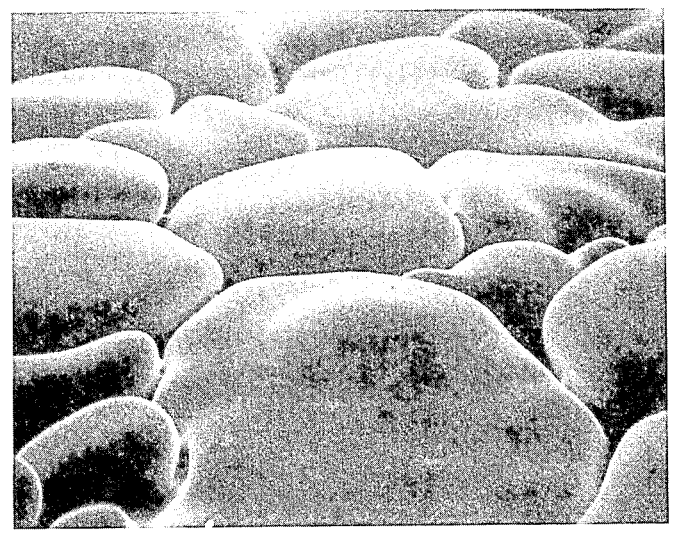
Figure 3A:
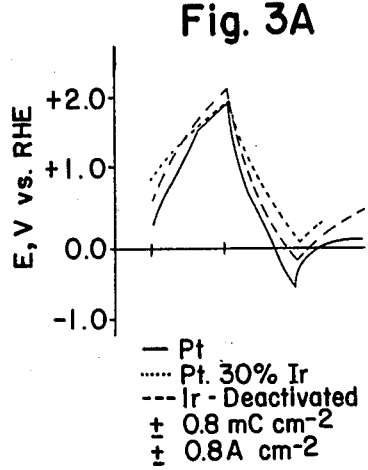
FIG. 3 compares the voltage response of uncoated electrodes in FIGS. 3A–3C and iridium oxide coated electrodes according to the invention in FIGS. 3D–3F to constant current pulses.
Figure 3D:
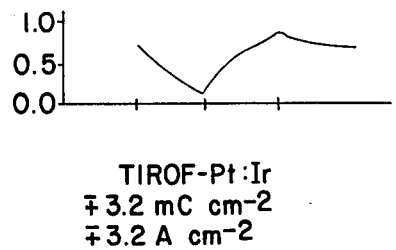
Figure 3B:
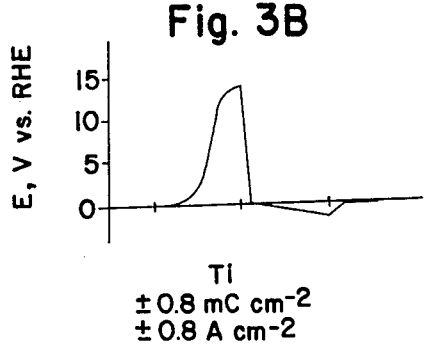
Figure 3E:
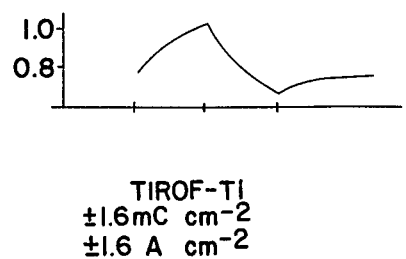
Figure 3C:
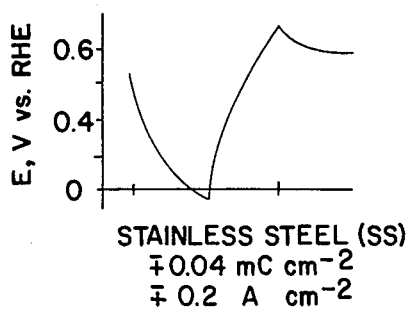
Figure 3F:
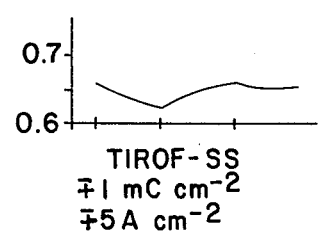

With reference now to the drawing and more particularly FIG. 1 thereof, there is shown a scanning electron microscope view of the surface of an uncoated electrode in FIG. 1A and in FIG. 1B an electrode according to the invention having a metallic layer carrying a surface coating of iridum oxide. Typically the diameter of the underlying metal electrode is 0.0025 inches and the iridium oxide coating is typically 0.00007 inches thick. An acceptable range of thickness is believed to be 0.00001 to 0.0001 inches.

The general feature of the invention is that a layer or iridium oxide is built up on the surface of a metallic stimulation electrode. Any metallic electrode may be used, e.g., Pt, Pt:Ir alloy, stainless steel alloys, Ti and its alloys, or Ta. A preferred method for applying the layer of iridium oxide is as follows:

1. An acid/alcohol solution containing dissolved iridium complex(es) is prepared by first heating $IrCl_3.3H_2O$ (Ir(III)trichloride) in 5.5M HCl (ca. 4% wt/vol) until 75-80% of the solution is evaporated. Heating the Ir(III) trichloride in the acid results in the conversion of the Ir(III) trichloride to a hexachloroiridate ion, $[IrCl_6]^{2-}$. The solution is restored to its initial volume with the addition of alcohol. Isopropyl alcohol and ethyl alcohol have both been used. This acid/alcohol solution is then aged for a period of time, e.g., 1-2 weeks, during which time the hexachloroiridate ion is slowly converted to a chloroiridate-alcohol complex of Ir(IV). The identification of said complex is presumptive and inferred from observed changes of the UV-visible absorption spectrum of the Ir containing solution with time.

2. The metallic electrode is soaked in the aged acid/alcohol solution of Ir for a prolonged period of time, typically 16 hours, after which it is dried for one hour at room temperature (22° C.) and annealed, in air, at 320° C. for 80-90 min. Prolonged soaking of the metallic electrode allows intimate association of the chloroiridate-alcohol complex(es) in solution with the surface of said metallic electrode so that the metallic surface becomes completely covered with the Ir complex(es). Shorter soaking times, e.g., of the order of minutes, leads to incomplete coverage of the metallic surface so that areas of uncoated metal remain exposed.

Successive layers are added by soaking the electrode in the acid/alcohol solution of Ir for 16-24 hours followed by 3-6 hours annealing at 320° C. after each period of soaking. Typically, 2-4 layers are applied. The high temperature annealing converts the chloroiridate-alcohol complex(es) deposited on the surface of the electrode to an oxide of Ir which is presumed to be $IrO_2$, $IrO_2.H_2O$, $Ir(OH)_4$ or combinations thereof. The precise molecular structure is not known at the present time. The annealing temperature of 320° C. was found to be optimum for obtaining highest charge injection capacity electrodes. The long annealing times are required for complete conversion of the chloroiridate-alcohol complex(es) to Ir oxide and the elimination of chloride from the film. Chloro- complexes of Ir which may remain on the surface due to insufficient annealing are susceptible to passing leaching and dissolution from the film. Moreover, insufficiently annealed films which contain a high chloride content have very low charge injection capacity due to the lesser proportion of the Ir(IV) oxide species which are responsible for the desired surface faradaic charge injection reactions.

3. The surface of the metallic electrode may be pretreated prior to deposition of the Ir solution to enhance the adhesion of the formed Ir oxide film. Such pretreatments include chemical or electrochemical etching and will vary depending upon the metallic electrode being coated.

Electrodes prepared in the described manner no longer have the electrochemical properties of the underlying metallic electrode as seen by cyclic voltammetry and illustrated in FIGS. 2A-2D. Instead, the voltammetric curves have the characteristics of IR oxide as is illustrated in FIGS. 2E-2H and retain these characteristics even after the Ir oxide coated electrodes have been used in in vitro stimulation tests over a prolonged period of time.

The voltage response of said Ir oxide coated electrodes to constant current pulses, such as are used for electrical stimulation of tissue, is an additional characteristic property with which to compare the charge injection capacity of Ir oxide coated electrodes with that of uncoated metallic electrodes. Comparative examples are shown in FIG. 3. In all examples, the magnitude of the voltage change across the Ir oxide interface in response to a constant current pulse shown in FIGS. 3D-3F was significantly less than the voltage change across the uncoated metallic electrode interface in response to the current pulse of the same magnitude shown in FIGS. 3A-3C.

The corrosion resistance conferred upon the metallic electrode by an Ir oxide coating was evaluated by analysis of test solutions for dissolution products of the metallic electrode. For instance, when Ir oxide coated Pt: 10% Ir electrodes were stimulated for 168 hours with biphasic, regulated current pulses, such as are used for electrical stimulation of tissue, no dissolution of the underlying Pt:Ir electrode was detected in the test solutions. This result was in marked contrast to the performance of electrodes on which the Ir oxide coating was absent. Non-Ir oxide coated Pt: 10% Ir electrodes lost between 2-8 μg of Pt during only 24 hours of in vitro stimulation under the same conditions as used for the Ir oxide coated electrodes.

There has been described novel structure and techniques for providing a high-charge capacity and a corrosion-resistant interface to metallic electrodes used to inject charge into biological tissue with controlled electrical pulses. It is evident that those skilled in the art may now make numerous uses and modifications of and departures from the specific structure and techniques described herein without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. The method of making a neural stimulator having an iridium oxide coated electrode which method includes the steps of, forming an acid/alcohol solution containing at least one dissolved iridium complex by heating Ir(III) trichloride in hydrochloric acid until more than half the solution is evaporated to convert the Ir(III) trichloride to a hexachloroiridate ion, $[IrCl_6]^{2-}$, adding alcohol to the solution following evaportion to restore the solution to its original volume, aging the restored acid/alcohol solution to slowly convert the hexachloroiridate ion to a chloroiridate-alcohol complex of Ir(IV), soaking said metallic electrode in the aged acid/alcohol solution for a prolonged period of time so that the electrode metallic surface becomes completely covered with the iridium complexes in the aged acid/alcohol, removing the covered metallic electrode from the aged acid/alcohol solution and drying the latter in air at room temperature, and annealing the dried coated electrode at a temperature sufficiently high for sufficient time to convert the chloroiridate-alcohol complexes deposited on the electrode surface to an oxide of iridium.

2. The method of claim 1 wherein said hydrochloric acid is 5.5M HCl (ca. 4% wt/vol) and the acid/alcohol solution is heated until 75-80% of the solution is evaporated.

3. A process in accordance with claim 1 wherein said alcohol is an alcohol from the group consisting of isopropyl alcohol and ethyl alcohol and said period of aging is of the order of 1-2 weeks.

4. A method in accordance with claim 1 wherein said prolonged period of time is of the order of 16 hours, the annealing temperature is of the order of 320° C. and the time of annealing is of the order of 80-90 minutes.

5. A method in accordance with claim 1 and further including the steps of adding successive layers by soaking the oxide-coated electrode in the aged acid/alcohol solution for of the order of 16-24 hours followed by annealing at of the order of 320° C. for of the order of 3-6 hours after each soaking.

6. A method in accordance with claim 1 and further including the step of etching the metallic electrode before immersion in said aged acid/alcohol solution to enhance the adhesion of the formed iridium oxide film.

* * * * *